United States Patent [19]
Toepel

[11] Patent Number: 5,992,417
[45] Date of Patent: Nov. 30, 1999

[54] PORTABLE, SELF-SUPPORTING, RIGID LASER CONTAINMENT BARRIER

[75] Inventor: Michael P. Toepel, Pittsfield, N.H.

[73] Assignee: Kentek Corporation, Pittsfield, N.H.

[21] Appl. No.: 09/033,273

[22] Filed: Mar. 2, 1998

[51] Int. Cl.⁶ .................................................. A61F 5/37
[52] U.S. Cl. .................... 128/846; 250/515.1; 250/516.1
[58] Field of Search .................... 128/849–856, 128/845, 846; 250/515.1, 516.1

[56] References Cited

U.S. PATENT DOCUMENTS

| | | | |
|---|---|---|---|
| 2,494,664 | 1/1950 | Lubow | 250/516.1 |
| 4,638,166 | 1/1987 | Baudro | 250/515.1 |
| 4,855,608 | 8/1989 | Peterson, II | 250/560 |
| 4,901,738 | 2/1990 | Brink et al. | 128/849 |
| 4,917,481 | 4/1990 | Koechner | 350/363 |
| 4,965,456 | 10/1990 | Huettenrauch | 250/515.1 |
| 5,151,095 | 9/1992 | Teeple, Jr. | 606/2 |
| 5,212,387 | 5/1993 | Swan | 250/515.1 |
| 5,220,175 | 6/1993 | Cole | 250/515.1 |
| 5,306,373 | 4/1994 | Swan | 156/242 |
| 5,469,864 | 11/1995 | Rosenblatt | 128/849 |

*Primary Examiner*—Michael A. Brown
*Attorney, Agent, or Firm*—Bourque & Associates, P.A.

[57] ABSTRACT

A personnel and equipment shield which includes at least one partition including a frame and a substantially rigid, high-power laser beam absorption panel affixed to the frame is provided. Each frame includes a base section upon which the barrier stands. In the preferred embodiment, the rigid laser beam absorption panels are a textured, laser absorption material, such as EVER-GUARD™ laser barrier material. In the preferred embodiment, the portable, self-supporting laser containment barrier is made up of at least two partitions, which are hingably attached to each other at adjacent sides thereof. Thus, the portable, self-supporting laser containment barrier can be set up in any number of positions. Finally, the base section of each partition may include rollers or casters to facilitate the positioning of the laser barrier as a whole or the positioning of the individual partitions with respect to each other.

9 Claims, 3 Drawing Sheets

PORTABLE, SELF-SUPPORTING, RIGID LASER CONTAINMENT BARRIER

FIELD OF THE INVENTION

The present invention relates to a laser containment barrier and, in particular, to a portable, self-supporting, rigid barrier, including a rigid frame and substantially rigid, high power laser beam absorption panels affixed to the frame and a base section upon which the barrier stands. More specifically, in the preferred embodiment, the rigid, high power laser beam absorption panels include a textured surface, which provides a plurality of convex dimples directed toward a source of laser radiation. These dimples aid in the diffusion of any errant laser radiation.

BACKGROUND OF THE INVENTION

It is becoming more and more common to use lasers to perform industrial, medical, and research procedures. It is well-known that the radiation from such lasers must be confined to certain operative areas and that lasers used under a variety of circumstances can present a danger to personnel and equipment. It is also well-known that it is difficult to totally prevent the occurrence of stray radiation in certain circumstances.

Personnel may be injured by direct exposure to a laser beam on the skin. Also, if a person's eyes were to become accidentally exposed to a laser beam, severe injury or loss of vision can occur. Since severe or even catastrophic injuries can occur due to exposure to errant laser radiation, many laser shields have been developed.

Most laser radiation barriers or shields consist of flexible, fabric-based materials, which are used to protect personnel from scattered and diffuse laser light. These, flexible shield materials can be used to construct protective clothing and/or drapes to be worn by or placed over personnel. Flexible materials can also be used to create curtains, which may be hung from any number of support devices in order to effectively contain an area within which a laser device is to be operated. However, due to their flexibility, these laser shield materials depends upon another structure to provide support.

Recently, rigid laser containment materials have begun to be used, especially in areas exposed to high-power laser radiation or direct hits from high-power laser beams. One such laser beam absorption material is known as EVER-GUARD™, which has been sold by the Kentek Corporation of Pittsfield, New Hampshire, the assignee of the present application for more than one year prior to the filing of the instant application. EVER-GUARD high power laser absorption panels comprise a textured surface, including a plurality of convexed dimples, which is directed toward a source of laser radiation. While EVER-GUARD panels have proven to be effective at containing high power laser radiation, they have, to date, simply been supported by existing flexible laser hanging systems, such as roller curtain tracks in areas susceptible to direct hits from high power radiation.

Also, since most flexible, laser containment curtains comprise a plurality of layers of material, they are relatively heavy and difficult to hang and reposition, if required.

Accordingly, it would be desirable to provide a portable, self-supporting laser containment barrier which includes a rigid frame, a substantially rigid, high power laser beam absorption panel affixed to the frame, and a base section upon which the barrier stands.

SUMMARY OF THE INVENTION

The present invention provides personnel and equipment shields which comprise a substantially rigid, high power laser beam absorption panels. The substantially rigid panels are affixed to substantially rigid frames which include base sections upon which the barriers stand. In the preferred embodiment, the rigid laser beam absorption panel is a textured material, such as EVER-GUARD laser barrier material. Furthermore, in the preferred embodiment, the portable, self-supporting rigid laser containment panel disclosed herein comprises at least two partitions each having a frame, substantially rigid laser beam absorption panel affixed to the frame, and a base section. The individual partitions are hingably attached to each other at one side thereof. Thus, the portable, self-supporting laser containment barrier can be set up in any number of positions. The base section of each partition may also include rollers or casters which would facilitate the positioning of the laser barrier as a whole or the positioning of the partitions thereof with respect to each other.

DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 1:
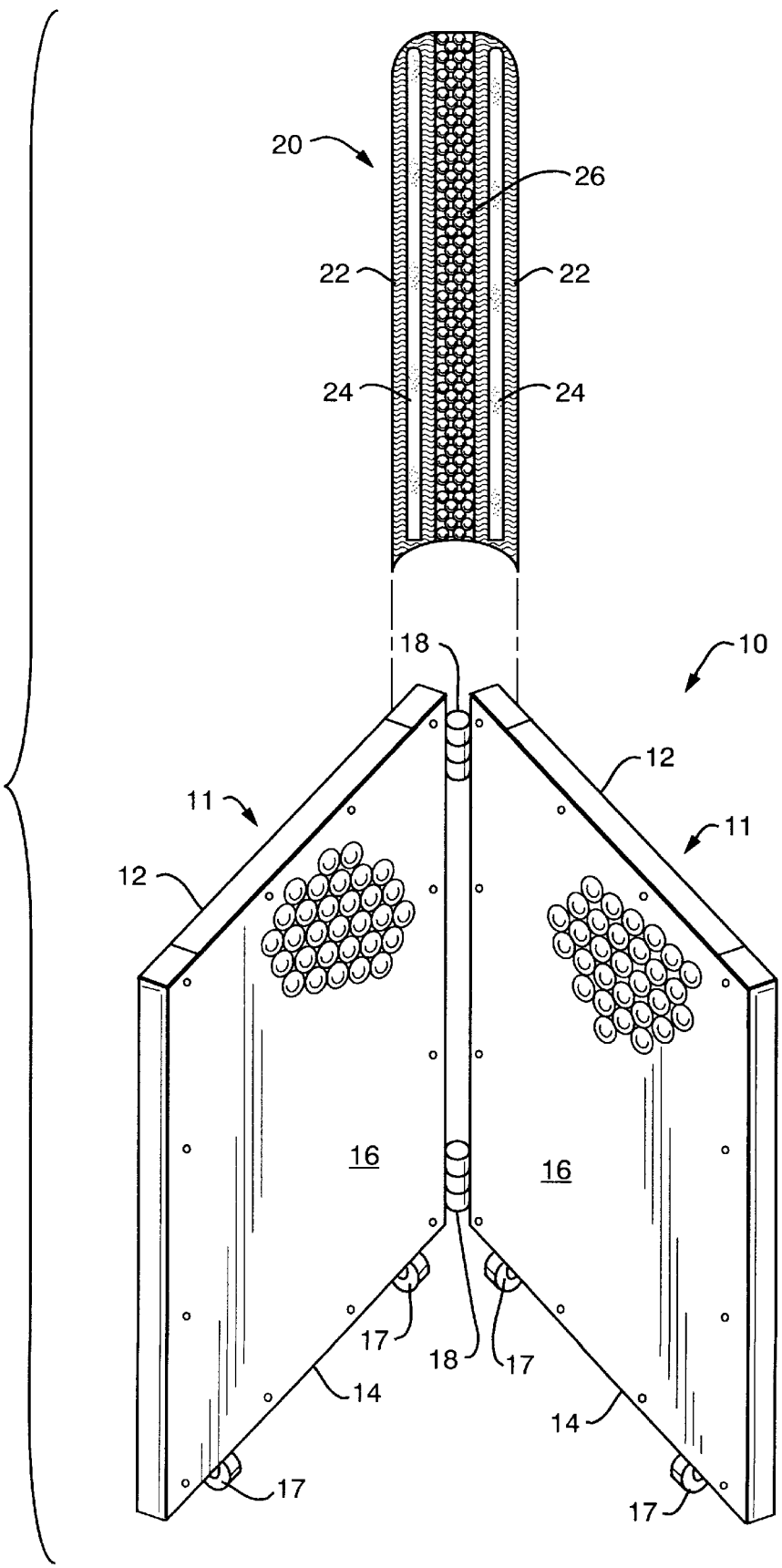
FIG. 1 is a front perspective view of the disclosed portable, self-supporting laser containment barrier.

A portable, self-supporting, laser containment barrier 10 is shown. Barrier 10 includes at least one partition 11. Each partition 11 includes a frame 12 having a substantially rigid laser beam absorption panel 16 affixed thereto. Each frame 12 has a base section 14 upon which the laser containment barrier stands. Base section 14 may further include additional support legs 15 to add stability to the structure caster or rollers 17, which would facilitate the movement and positioning of the laser containment barrier, or both.

The substantially rigid, high power laser beam absorption panel 16, which is affixed to the frame 12 of each partition 11 is preferably a metallic sheet material and, more specifically, aluminum, due to weight considerations. The metallic laser beam absorption panel may further be textured and/or coated with a substantially black coating in order to aid in the diffusion and/or absorption of high power laser radiation.

Each laser beam absorption panel 16 is fastened to its frame 12 using any type of suitable type fastener, such as screws or rivets. The laser beam absorption panel 16 may also be chemically bonded to the frame 12 or even welded thereto.

In the preferred embodiment, the substantially rigid laser beam absorption panels are EVER-GUARD panels, which are sold by Kentek Corporation of Pittsfield, New Hampshire. EVER-GUARD panels are specially designed, textured aluminum barriers which feature an absorbing, substantially black matte finish. Thus, an unfocused, direct laser beam will be blocked by an EVER-GUARD panel indefinitely with minimal effects to the laser containment barrier.

Figure 2:
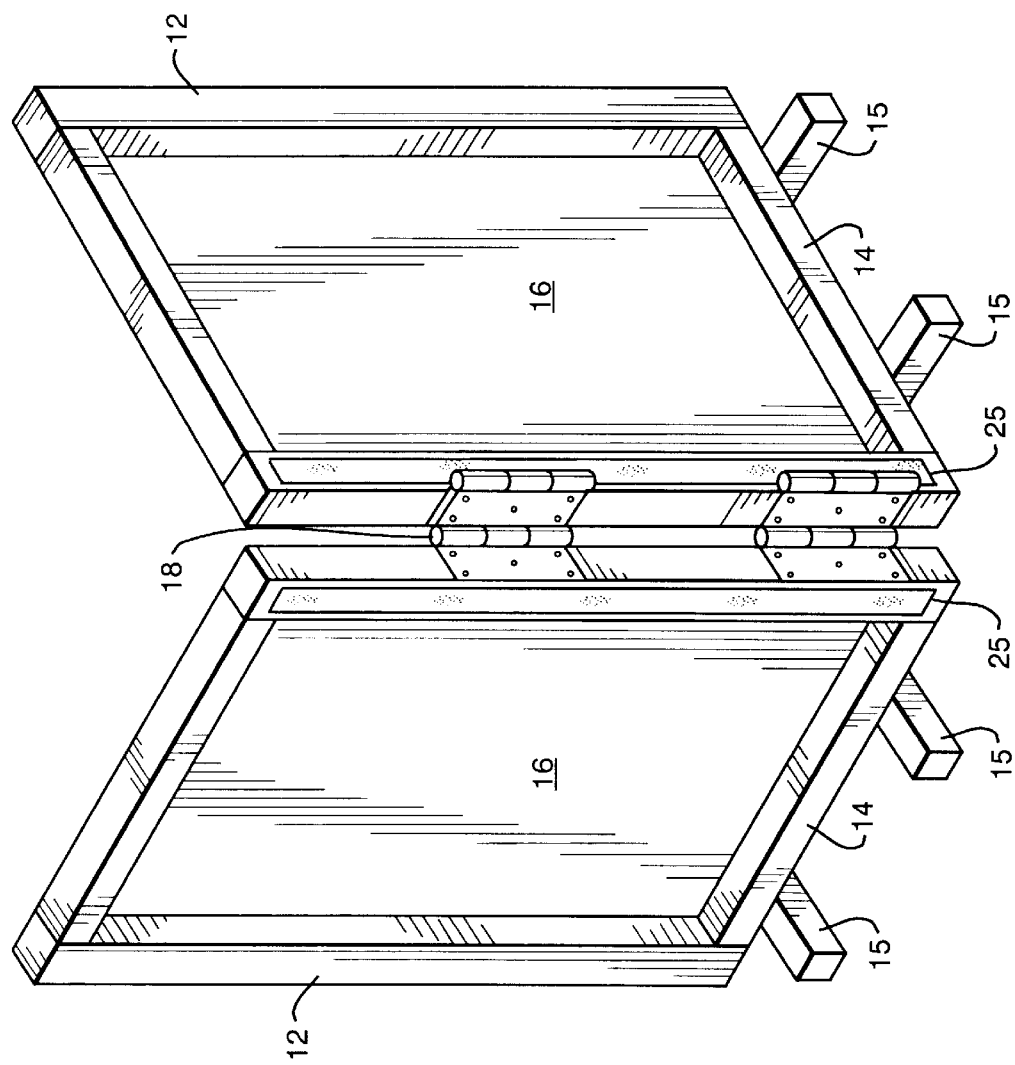
FIG. 2 is a back view of the disclosed portable, self-supporting laser containment barrier.
Figure 3:
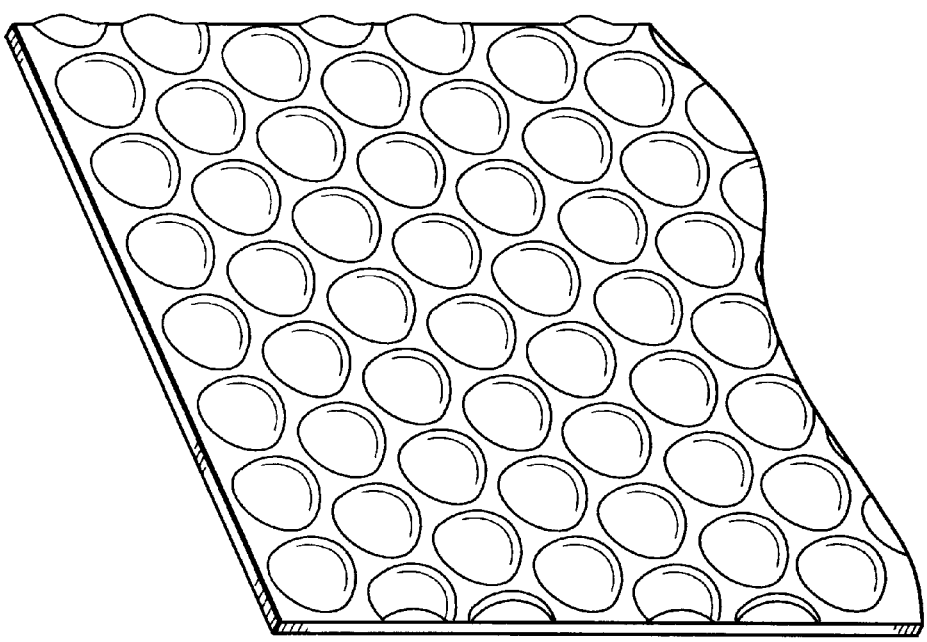
FIG. 3 is a close up view of the substantially rigid laser beam absorption material of FIG. 1.

As shown in FIGS. 1 and 2, multiple partitions 11 may be hingably attached to each other using a plurality of hinges 18. While the following description will refer to an embodiment including two partitions, any number of partitions may be hingably attached to each other in order to create portable, self-supporting laser containment barriers of differing sizes. As will be more fully discussed below, the use of bi-directional hinges will allow any number of partitions to be folded into a compact area when the laser containment barrier is not in use.

Bi-directional hinges allow each partition to be positioned substantially 360° (degrees) with respect to an adjacent partition. Thus, complex arrangements of barriers can be created using multi-partitioned barrier systems. Additionally, structural rigidity can be attained by un-folding and positioning a barrier system into a "zig-zag" pattern.

Another important feature of the disclosed invention is light strip 20, which effectively seals the hinge area between two adjacent partitions to prevent errant laser radiation from passing therethrough. Light strip 20 includes a flexible fabric backing 22, which is substantially the same length as each partition is tall. Each light strip has a first and second end, each of which has a fastening system 24 attached thereto. In the preferred embodiment, the fastening system 24 includes hook and loop fasteners as sold under the trademark, VELCRO. Disposed on each partition frame 12, proximate each hinge area is a corresponding fastener 25, which, in the preferred embodiment, would be a corresponding VELCRO hook and loop fastener strip. Thus, the light strip may be removably fastened to each partition 11 to seal each hinge section.

The benefit of using a flexible fabric backing allows the laser containment barrier partitions to be re-positioned with respect to each even after the light strip is attached thereto. It also allows light strips of a single configuration to be used in conjunction with relative partition angular positions ranging from 0–360° (degrees).

In order to provide optimum high power laser absorption capabilities, even in the hinge area, intermediate the first and second end of the light strip is a strip of substantially rigid laser beam absorption material 26, such as EVER-GUARD. The EVER-GUARD strip 26 is substantially identical to the EVER-GUARD panels described earlier. Namely, it is a textured aluminum barrier material, which features a plurality of convex dimples, which are oriented toward a source of laser radiation. In addition, like the EVER-GUARD panels, the EVER-GUARD strips 26 feature an absorbing black matte finish which absorbs the laser radiation.

Modifications and substitutions by one of ordinary skill in the art are considered to be within the scope of the present invention which is not to be limited except by the claims which follow.

What is claimed is:

1. A portable, self-supporting, laser containment barrier comprising at least two partitions, each of said partitions having a frame, a substantially rigid laser beam absorption panel affixed to said frame, said partitions hingably attached to each other at adjacent sides using hinges, each said frame further having a base section upon which said barrier stands.

2. The portable, self-supporting, laser containment barrier as claimed in claim 1, wherein said hinges are bi-directional hinges allowing each said partition to be positioned at any angle with respect to an adjacent partition.

3. The portable, self-supporting, rigid laser containment barrier as claimed in claim 1, further comprising a light strip disposed intermediate said adjacent sides of said partitions to contain any stray laser radiation directed intermediate said adjacent partitions, said light strip comprising a flexible membrane removably attached to each partition at first and second ends and a strip of substantially rigid laser beam absorption material affixed to said membrane intermediate said first and second ends, said strip of rigid laser beam absorption material effectively sealing said hinge area and preventing the transmission of laser radiation therethrough.

4. The portable, self-supporting, rigid laser containment barrier as claimed in claim 1, further comprising rollers affixed to said base side of each of said partitions to allow said partitions to be rolled into position in conjunction with and independent of each other.

5. The portable, self-supporting, rigid laser containment barrier as claimed in claim 1, wherein each said rigid laser beam absorption panel comprises a textured panel having a plurality of convex dimples on a first face thereof.

6. The portable, self-supporting, rigid laser containment barrier as claimed in claim 5, wherein said textured panel material is coated with a substantially black coating on at least one surface thereof.

7. The portable, self-supporting, rigid laser containment barrier as claimed in claim 1, wherein said rigid laser beam absorption material comprises a metallic sheet material.

8. The portable, self-supporting, rigid laser containment barrier as claimed in claim 1, wherein said metal sheet material is aluminum.

9. The portable, self-supporting, rigid laser containment barrier as claimed in claim 1, wherein said rigid laser beam absorption material is coated on at least one side thereof with a substantially black coating.

* * * * *